United States Patent
Iyer et al.

(10) Patent No.: US 9,095,471 B2
(45) Date of Patent: Aug. 4, 2015

(54) PRE-EMPTIVE FLUID SHIFTS TO TREAT OBSTRUCTIVE SLEEP APNEA

(75) Inventors: Vijay Kumar Iyer, Export, PA (US); Erik Kurt Witt, Murrysville, PA (US)

(73) Assignee: Koninklijke Philps N.V., Eindhoven (NL)

( * ) Notice: Subject to any disclaimer, the term of this patent is extended or adjusted under 35 U.S.C. 154(b) by 809 days.

(21) Appl. No.: 13/265,502

(22) PCT Filed: Mar. 15, 2010

(86) PCT No.: PCT/IB2010/051118
§ 371 (c)(1),
(2), (4) Date: Oct. 20, 2011

(87) PCT Pub. No.: WO2010/122435
PCT Pub. Date: Oct. 28, 2010

(65) Prior Publication Data
US 2012/0157900 A1     Jun. 21, 2012

Related U.S. Application Data

(60) Provisional application No. 61/172,389, filed on Apr. 24, 2009.

(51) Int. Cl.
*A61H 9/00* (2006.01)
*A61F 13/08* (2006.01)
*A61N 1/04* (2006.01)
*A61N 1/36* (2006.01)

(52) U.S. Cl.
CPC ........... *A61F 13/08* (2013.01); *A61N 1/0456* (2013.01); *A61N 1/36014* (2013.01)

(58) Field of Classification Search
CPC ... A61F 13/08; A61N 1/36014; A61N 1/0456
USPC ................... 601/148–152; 128/898
See application file for complete search history.

(56) References Cited

U.S. PATENT DOCUMENTS

| | | | |
|---|---|---|---|
| 4,039,039 A | 8/1977 | Gottfried |
| 4,270,527 A | 6/1981 | Peters et al. |
| 4,355,632 A | 10/1982 | Sandman |
| 4,577,622 A | 3/1986 | Jennings |
| 4,614,179 A | 9/1986 | Gardner et al. |
| 4,614,180 A | 9/1986 | Gardner et al. |
| 4,696,289 A | 9/1987 | Gardner et al. |
| 4,702,232 A | 10/1987 | Gardner et al. |
| 4,841,956 A | 6/1989 | Gardner et al. |
| 5,651,792 A | 7/1997 | Telikicherla |

(Continued)

FOREIGN PATENT DOCUMENTS

JP       2008520306 A      6/2008

OTHER PUBLICATIONS

Redolfi et al. 's Article "Relationship between Overnight Rostral Fluid Shift and Obstructive Sleep Apnea in Nonobese Men", American Journal of Respiratory and Critical Care Medicine, vol. 179, No. 3 (Originally Published in Press as DOI: 10.1164/rccm.200807-1076OC on Nov. 14, 2008), pp. 241-246.*

(Continued)

*Primary Examiner* — Quang D Thanh

(57) ABSTRACT

A method of treating obstructive sleep apnea comprising reducing an effective amount of extracellular fluid of a patient suffering from obstructive sleep apnea.

10 Claims, 1 Drawing Sheet

(56) References Cited

U.S. PATENT DOCUMENTS

| | | |
|---|---|---|
| 5,653,244 A | 8/1997 | Shaw |
| 5,711,760 A * | 1/1998 | Ibrahim et al. ............ 601/149 |
| 6,338,723 B1 | 1/2002 | Carpenter et al. |
| 6,589,194 B1 * | 7/2003 | Calderon et al. ........... 601/151 |
| 6,592,534 B1 | 7/2003 | Rutt et al. |
| 6,613,007 B1 | 9/2003 | Reid |
| 6,615,080 B1 | 9/2003 | Unsworth et al. |
| 6,736,787 B1 | 5/2004 | McEwen et al. |
| 7,001,384 B2 | 2/2006 | Berish et al. |
| 7,187,973 B2 | 3/2007 | Hauck |
| 7,207,959 B1 | 4/2007 | Chandran |
| 7,499,748 B2 | 3/2009 | Moffitt et al. |
| 2003/0176822 A1 * | 9/2003 | Morgenlander ............ 601/152 |
| 2004/0030270 A1 * | 2/2004 | Johnson .................... 601/15 |
| 2009/0234265 A1 * | 9/2009 | Reid et al. ................. 602/61 |
| 2012/0041513 A1 | 2/2012 | Tucker et al. |

OTHER PUBLICATIONS

Chiu et al, "Fluid Shift by Lower Body Positive Pressure Increases Pharyngeal Resistance in Healthy Subjects", American Journal of Respiratory and Critical Care Medicine, vol. 174, 2006, pp. 1378-1383.

Redolfi et al, "Relationship Betweenovernight Rostral Fluid Shift and Obstructive Sleep Apnea in Nonobese Men", American Journal of Respiratory and Critical Care Medicine, vol. 179, 2009, pp. 241-246.

Lettieri et al, "Pneumatic Compression Devices Are an Effective Therapy for Restless Legs Syndrome", American College of Chest Physicians, vol. 135, No. 1, Jan. 2009, pp. 74-80.

Redolfi et al, "Association Between Overnight Rostral Fluid Shift and Obstructive Sleep Apnea", American Journal of Respiratory and Critical Care Medicine, vol. 177, Ontario, Canada 2008, p. 484A.

* cited by examiner

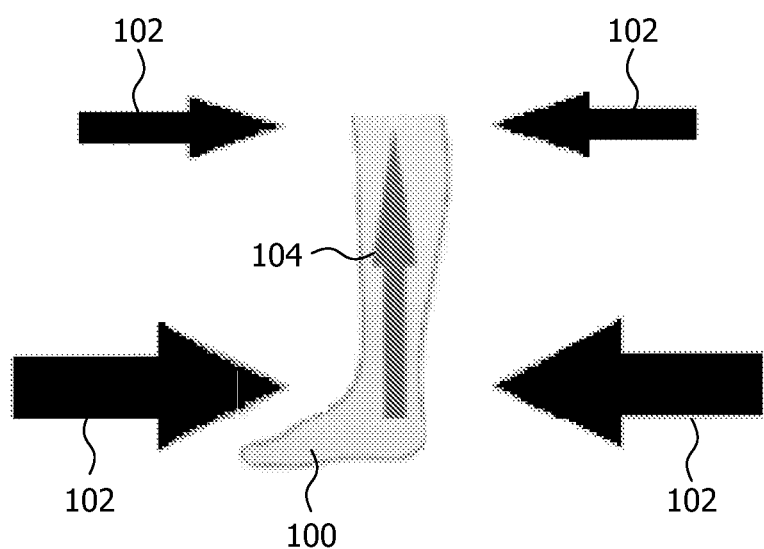

PRE-EMPTIVE FLUID SHIFTS TO TREAT OBSTRUCTIVE SLEEP APNEA

This application claims benefit under 35 U.S.C. §119(e) of U.S. Provisional Application No. 61/172,389 filed on Apr. 24, 2009, the contents of which are herein incorporated by reference.

The present invention pertains to methods of treating obstructive sleep apnea and in particular to treating obstructive sleep apnea by shifting fluids from the lower extremities of the body prior to sleep.

Gravity dependent fluid shifts from postural changes typically lead to significant changes in weight distribution and intra and extra vascular fluid volume distributions. These changes can be a significant detriment of upper airway dynamics and lead to obstructive apnea events during sleep. Movement of fluid from the legs in non-obese subjects has been shown to lead to an increase in neck circumference, reduced upper airway caliber and increased collapsibility. Further, it has been suggested that among non-obese subjects, the Apnea-Hypopnea Index (AHI) in sleep may be caused by nocturnal fluid volume shifts from the legs to the neck. These fluid volume shifts, in turn, are related to sedentary living during the day.

Sedentary living leads to venous stasis in the legs during the day. Upon reclining to sleep, the fluid in the legs shifts and increases the fluid volumes in the rostral areas. The increased fluid volumes in the rostral areas, in turn, leads to an the increase in neck circumference, reduced airway caliber and increased collapsibility of the upper airways. These in turn cause obstructive events during sleep characteristic of obstructive sleep apnea (OSA).

It would therefore be advantageous to have a method of treating OSA by managing the shift of fluids in the body which lead to OSA.

Accordingly, it is an object of the present invention to provide methods of treating obstructive sleep apnea that overcomes the shortcomings of the conventional methods. This object is achieved according to one embodiment of the present invention by providing a method that includes reducing an effective amount of extracellular fluid of a patient suffering from obstructive sleep apnea.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

The attached FIGURE is a schematic illustration of an embodiment of the invention.

Embodiments of the present invention relate to methods of treating obstructive sleep apnea. Specifically, various embodiments are related to reducing an effective amount of extracellular fluid of a patient suffering from obstructive sleep apnea sufficient to reduce or eliminate the obstructive sleep apnea. In one embodiment, reducing an effective amount of extracellular fluid comprises applying compression to the lower extremities of the patient. In another embodiment, compression is applied at least 1 hour prior to lying down to sleep. In another embodiment, compression is applied for at least 20 minutes. Preferably, compression is applied with a pneumatic compression device, a device that employing electrically activated materials, a device that uses mechanical actuators that constrict bands around the extremities, passive elastic garments, or antishock trousers.

Another embodiment comprises elevating the legs of the patient above the heart of the patient. Still another embodiment comprises applying electrical stimulation to the patient. In one aspect, the electrical stimulation is applied with a transcutaneous electrical nerve stimulator. In another embodiment, the method further relieves symptoms of restless leg syndrome. Still anther embodiment comprises administering a diuretic to the patient. Another embodiment comprises sensing the reduction in amount of extracellular fluid. Another embodiment comprises ending a treatment based on a sensed reduction in the extracellular fluid.

Typically, the heart attempts to pump blood against gravity up the veins of the legs. As a person walks, the regular contraction and relaxation of the calf muscles around the veins help the heart move blood up the legs efficiently. It is unlikely, however, that a typical person walks continuously throughout the day—most people sit or stand some of the time. Additionally, some people have inherited weakness of the vein walls or valves, which create additional challenges to venous circulation.

Obstructive sleep apnea, as first appreciated by the inventors, may be caused by the timing of the back shift of extracellular fluid from the lower extremities of a patent to the rostral areas during sleep. If the fluids, however, are shifted from the lower extremities earlier in the day (prior to going to sleep) the fluids could circulate and distribute over the body. In this manner, excess fluid can be eliminated and therefore be less likely to collect and increase rostral fluid volumes. The shift of fluid from the lower extremities can be accomplished, for example, by using compression therapy to move the fluid, applying pressure to the lower body with anti shock trousers, or exercising the lower body before sleep.

The use of compression therapy to shift fluid from the lower extremities is illustrated in the FIGURE. Pressure 102 is applied to leg 100. The pressure 102 causes extracellular fluid 104 to flow from the leg 100 into the upper body (not shown). Preferably, the treatment is performed at least a half hour before the patient going to sleep. In alternative embodiments of the invention, the treatment is performed at least one hour before the patient going to sleep. In another alternative embodiment of the invention, the treatment is performed at least two hours before the patient going to sleep. In another alternative embodiment of the invention, the treatment is performed at least four hours before the patient going to sleep. Sufficient time should be provided to shift the fluid from the extracellular space into the circulation. This will, in turn, reduce the amount of fluid that shifts into the tissues surrounding the upper airway at night, when the patient is in a reclining position.

Persons susceptible to fluid collection during the day due to a sedentary lifestyle, can reduce the chances of having obstructive events by moving the fluid back to the upper parts of the body before sleep. In one embodiment of the invention, excess fluid is eliminated by the renal system. If the fluid regulation systems of the body detect an increased fluid load because of a shift out of the lower extremities before sleep, there will be increased diuresis of those fluids. Further, fluid elimination from the body can be enhanced by administering a diuretic to the patient.

Various devices can be employed to facilitate the fluid shift from the lower extremities to the upper body. Example devices include, but are not limited to:

pneumatic compression devices (PCDs),
devices that employing electrically activated materials, such as EPAM (electrically active polymers),
devices using mechanical actuators (motors, solenoids, etc) that would constrict bands around the extremities,
passive elastic garments which provide a more continuous pressure on the extremities, such as a sock-like garment with elastic fibers or bands along the perimeter,
devices similar to anti-shock trousers,
devices that help raise the legs above the heart of the patient, and
a venous stasis pump (i.e. Aircast Venaflow), and
devices that use electrical stimulation directly (i.e. Transcutaneous Electrical Nerve Stimulator or TENS) to cause fluid shifts from the legs.

Known devices which can be used in conjunction with the methods of the present application have been described in the following patents, the contents of which are hereby incorporated by reference in their entirety: pneumatic—U.S. Pat. Nos. 5,651,792; 4,841,956; 4,614,179; 4,614,180; 4,702,232; 6,592,534, anti-shock trousers—U.S. Pat. Nos. 4,577,622; 4,355,632; 4,270,527; 4,039,039, elastic garments—U.S. Pat. Nos. 6,613,007; 6,338,723; 5,653,244, venous stasis pumps U.S. Pat. Nos. 7,207,959; 7,001,384, 6,736,787, constriction bands—U.S. Pat. No. 4,696,289, TENS/electrical stimulation—U.S. Pat. Nos. 6,615,080; 7,499,748; 7,187,973. Other devices known to those of ordinary skill in the art may used as well. Additionally, some patients may be able to take a walk or exercise to move the fluids back. Further, some patients may find it effective to just put their feet up or lay down without sleeping.

In another embodiment, the devices and methods discussed above may be combined with the therapy for restless leg syndrome (RLS) patients who have fluid shift based obstructive sleep apnea. Pneumatic compression devices have been shown to be effective in relieving symptoms of RLS in the early evening. Thus, the combination of therapies would be advantageous to those patients suffering from both RLS and OSA.

In another embodiment, the fluid transfer system may be combined with a sensor to determine the efficacy of fluid shift. There are a number of sensor devices, including those employing electrical impedance, to accomplish this. In one aspect, the sensor system determines whether sufficient fluid shift has occurred to determine the end of a therapy session.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method of treating obstructive sleep apnea comprising:
   reducing, with a reducing treatment, an effective amount of extracellular fluid of a patient suffering from obstructive sleep apnea;
   sensing, with electrical impedance, an efficacy of fluid shift and an associated reduction in the effective amount of extracellular fluid in the patient caused by the reducing treatment;
   controlling a duration of the reducing treatment based on the sensing; and
   ending the reducing treatment based on a sensed reduction in the effective amount of extracellular fluid.

2. The method of claim 1, wherein reducing, with the reducing treatment, an effective amount of extracellular fluid comprises applying compression to the lower extremities of the patient.

3. The method of claim 2, wherein compression is applied at least 1 hour prior to lying down to sleep.

4. The method of claim 2, wherein compression is applied for at least 20 minutes.

5. The method of claim 2, wherein compression is applied with a pneumatic compression device, a device that employing electrically activated materials, a device that uses mechanical actuators that constrict bands around the extremities, passive elastic garments, or antishock trousers.

6. The method of claim 1, wherein the reducing treatment comprises elevating the legs of the patient above the heart of the patient.

7. The method of claim 1, wherein the reducing treatment comprises applying electrical stimulation to the patient.

8. The method of claim 7, wherein electrical stimulation is applied with a transcutaneous electrical nerve stimulator.

9. The method of claim 1, wherein the method further relieves symptoms of restless leg syndrome.

10. The method of claim 1, further comprising administering a diuretic to the patient.

\* \* \* \* \*